US011919907B2

(12) United States Patent
Silverman et al.

(10) Patent No.: US 11,919,907 B2
(45) Date of Patent: Mar. 5, 2024

(54) DEUTERATED JAK INHIBITOR AND USES THEREOF

(71) Applicant: Sun Pharmaceutical Industries, Inc., Princeton, NJ (US)

(72) Inventors: I. Robert Silverman, Arlington, MA (US); Changhua Liu, Carlisle, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 0 days.

(21) Appl. No.: 17/327,044

(22) Filed: May 21, 2021

(65) Prior Publication Data

US 2021/0387991 A1    Dec. 16, 2021

Related U.S. Application Data

(60) Provisional application No. 63/028,378, filed on May 21, 2020.

(51) Int. Cl.
*C07D 487/04* (2006.01)
*A61K 45/06* (2006.01)

(52) U.S. Cl.
CPC ............ *C07D 487/04* (2013.01); *A61K 45/06* (2013.01); *C07B 2200/05* (2013.01)

(58) Field of Classification Search
CPC .... C07D 487/04; A61K 45/06; C07B 2200/05
USPC ...................................................... 514/265.1
See application file for complete search history.

(56) References Cited

U.S. PATENT DOCUMENTS

| 9,000,161 | B2 | 4/2015 | Zhou et al. | |
| 9,249,149 | B2 * | 2/2016 | Silverman | A61K 31/7068 |
| 9,662,335 | B2 | 5/2017 | Rodgers et al. | |
| 10,561,657 | B2 * | 2/2020 | Zhu | C07D 487/04 |
| 10,561,659 | B2 | 2/2020 | Wagner et al. | |
| 2022/0213105 | A1 | 7/2022 | Lewis et al. | |
| 2022/0306636 | A1 | 9/2022 | Lewis et al. | |
| 2023/0322787 | A1 | 10/2023 | Wiedemann et al. | |

FOREIGN PATENT DOCUMENTS

| CN | 107759623 A | 3/2018 |
| CN | 107915738 A | 4/2018 |
| EP | 3398952 A1 | 11/2018 |
| WO | WO-2007/070514 A1 | 6/2007 |
| WO | WO-2010/038434 A1 | 4/2010 |
| WO | WO-2010/083283 A2 | 7/2010 |
| WO | WO-2013/188783 A1 | 12/2013 |
| WO | WO-2017/192905 A1 | 11/2017 |
| WO | WO-2020/163653 A1 | 8/2020 |
| WO | WO-2021/236139 A1 | 11/2021 |
| WO | WO-2022/036030 A1 | 2/2022 |

OTHER PUBLICATIONS

International Search Report and Written Opinion for International Application No. PCT/US2020/017093 dated Apr. 30, 2020.
International Search Report and Written Opinion for International Application No. PCT/US2020/045977 dated Feb. 5, 2021.
Shiner et al., "Deuterium isotope effects for migrating and nonmigrating groups in the solvolysis of neopentyl-type esters," Journal of the American Chemical Society, 103(2): 436-442 (1981).
Zhang et al., "An improved synthesis of 4-chloro-7H-pyrrolo[2,3-d]pyrimidine," Chemistry of Heterocyclic Compounds, 54: 638-642 (2018).
International Search Report and Written Opinion for International Application No. PCT/US2021/045652 dated Oct. 29, 2021.
U.S. Appl. No. 18/020,869, "Process for Preparing Enantiomerically Enriched JAK Inhibitors," filed Feb. 10, 2023.
Shafer, "Chapter 6: Nitrile reactivity" in *The Chemistry of the cyano group*, Z. Rappoport, ed., (1970).
Snyder et al., "Polyphosphoric Acid as a Reagent in Organic Chemistry. VI. The Hydrolysis of Nitriles to Amides" J. Am. Chem. Soc., vol. 76, pp. 3039-3040 (1954).
21.5: Hydrolysis of nitriles <https://chem.libretexts.org/Courses/SUNY_Potsdam/Book%3A_Organic_Chemistry_II_(Walker)/21%3A_Nucleophilic_Addition_of_Weak_Nucleophiles/21.05%3A_Hydrolysis_of_nitriles> Retrieved On Line Oct. 17, 2023.
Berger et al., "Une Nouvelle Methode de Saponification des Amides et des Nitriles" Ann.Chim, vol. 46, No. 8, p. 600-604 (1927).
Cason et al., "Branched-Chain Fatty Acids. XXVII. Further Study of the Dependence of Rate of Amide Hydrolysison Substitution Near the Amide Group Relativerates of Hydrolysis of Nitrile To Amide and Amide To Acid" J. Org. Chem. vol. 18, No. 9, p. 1129-1136 (1953).

(Continued)

*Primary Examiner* — Yevgeny Valenrod
(74) *Attorney, Agent, or Firm* — FOLEY HOAG LLP

(57) ABSTRACT

Disclosed is a JAK1 and/or JAK2 inhibitor of the following structural formula:

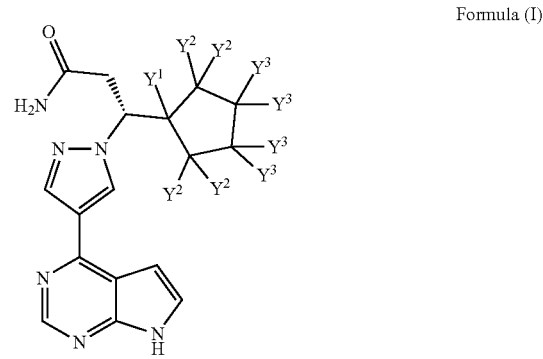

Formula (I)

or a pharmaceutically acceptable salt thereof. This invention also provides pharmaceutical compositions comprising a compound of Formula (I), optionally including additional therapeutic agents, and use in methods of treatment for hair loss disorders.

24 Claims, No Drawings

(56) References Cited

OTHER PUBLICATIONS

Hydrolysis of nitriles: Amide vs Carboxylic acid <https://chemistry.stackexchange.com/questions/150031/hydrolysis-of-nitriles-amide-vs-carboxylic-acid> Retrieved On Line Oct. 17, 2023.
Jensen et al., "Kinetics and Mechanism of Nitrile Hydration Catalyzed by Unhindered Hydridobis (phosphine) platinum (II) Complexes. Regioselective Hydration of Acrylonitrile" J.Am.Chem.Soc, vol. 108, p. 723-729 (1986).
Krieble et al., "The Hydrolysis of Nitriles with Acids" JACS, vol. 61, p. 560-563 (1939).
Magat et al., Acid-catalyzed Reactions of Nitriles. I. The Reaction of Nitriles with Formaldehyde, vol. 73, No. 3, p. 1028-1031 (1951).
Meier, "Triphenylphosphine Hydrobromide" EROS, DOI: 10.1002/047084289X (2001).
Miocque et al., "Addition des reactifs nucleophiles sur la triple liaison nitrile." Ann. Chim , vol. 5, p. 11-22. (1970).
Phind V4 Model <https://www.phind.com/search?cache=mdfsymlxm2bc4omvjmkwpr5t> Retrieved On Line Oct. 17, 2023.
Rabinovitch et al., "The Hydrolysis Of Aliphatic Nitriles In Concentrated Hydrochloric Acid Solutions " Canadian Journal of Research, vol. 20b, No. 10 (1942).
Ripin and Evans <http://ccc.chem.pitt.edu/wipf/MechOMs/evans_pKa_table.pdf> Retrieved On Line Oct. 17, 2023.
Zil'berman, "Reactions of Nitriles With Hydrogen Halides and Nucleophilic Reagents," Russ. Chem. Rev. 31, 615 (1962).

* cited by examiner

DEUTERATED JAK INHIBITOR AND USES THEREOF

RELATED APPLICATIONS

This application claims the benefit of priority to U.S. Provisional Patent Application No. 63/028,378, filed May 21, 2020, the contents of which are incorporated herein by reference in their entirety.

BACKGROUND OF THE INVENTION

Janus Kinases (JAKs) JAK1, JAK2, JAK3, and TYK2 are signaling proteins that are dysregulated in various autoimmune, inflammatory and cancer diseases. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Several JAK inhibitors have been approved and are currently in clinical trials. Examples of JAK inhibitors include the approved drugs ruxolitinib, baricitinib, and tofacitinib among others. Drug candidates in clinical trials include, inter alia, filgotinib, momelotinib and pacritinib. These JAK inhibitors may differ according to the selectivity against different JAK subtypes. Whereas ruxolitinib and baricitinib are selective dual inhibitors of JAK1 and JAK2, tofacitinib is selective for the JAK3 subtype. JAK inhibitors have reported utility for various cancer and autoimmune diseases. Ruxolitinib is currently approved for the treatment of patients with intermediate or high-risk myelofibrosis, including primary myelofibrosis, post-polycythemia vera myelofibrosis, post-essential thrombocythemia myelofibrosis, and steroid-refractory acute graft-versus-host disease, and is in clinical trials for various other conditions. Tofacitinib and baricitinib are approved for rheumatoid arthritis.

Another selective JAK1 and JAK2 inhibitor is CTP-543 (also referred to as (R)-3-(4-(7H-pyrrolo[2,3-d]pyrimidin-4-yl)-1H-pyrazol-1-yl)-3-(cyclopentyl-2,2,3,3,4,4,5,5-ds)propanenitrile, or D8-ruxolitinib). CTP-543 phosphate is currently in clinical trials for hair-loss disorders, including alopecia areata (AA) and has demonstrated significant activity in treating AA, compared to placebo. CTP-543 is represented by the following structural formula:

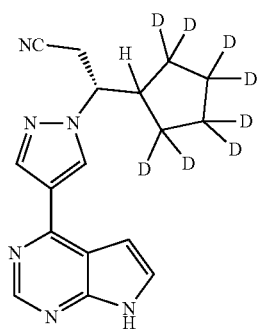

CTP-543

Despite the beneficial activities of JAK inhibitors, there is a continuing need for new compounds to treat the aforementioned diseases and conditions.

SUMMARY OF INVENTION

It has now been found that certain novel compounds have activity as selective JAK1 and JAK2 inhibitors. These selective JAK inhibitors are useful in treating autoimmune, inflammatory and cancer diseases mediated by dysregulation of JAK activity such as rheumatoid arthritis, myelofibrosis, polycythemia vera, alopecia areata and graft versus host disease, among others. These selective JAK inhibitors are represented by the following structural formula:

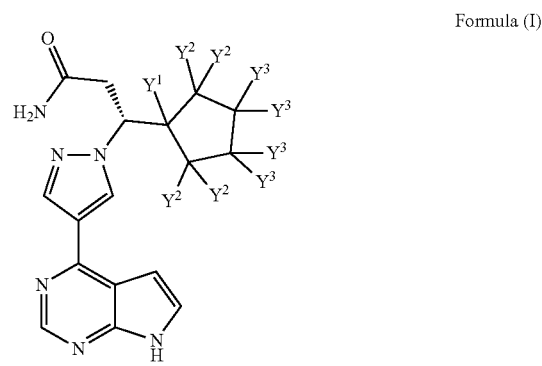

Formula (I)

wherein $Y^1$ is selected from hydrogen and deuterium; each $Y^2$ is selected from hydrogen and deuterium; and each $Y^3$ is selected from hydrogen and deuterium. In certain embodiments, each $Y^2$ is the same. In certain embodiments, each $Y^3$ is the same. In certain embodiments, at least one of $Y^1$, $Y^2$, and $Y^3$ is deuterium. In certain embodiments, each $Y^2$ is deuterium. In certain embodiments, each $Y^3$ is deuterium. In certain embodiments, each $Y^2$ and each $Y^3$ is deuterium. In certain embodiments, each position designated specifically as deuterium has at least 90%, at least 95%, at least 97%, at least 98%, or at least 99% incorporation of deuterium.

Specific examples of compounds of Formula (I) include the following:

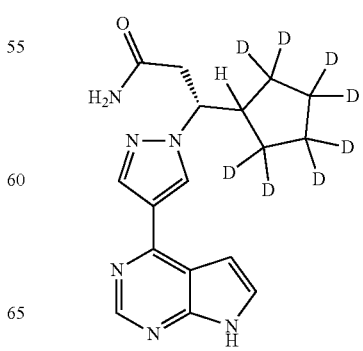

10

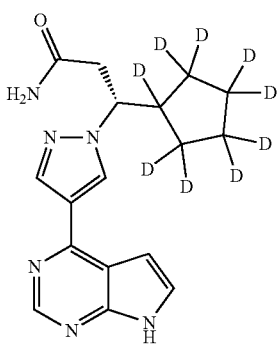

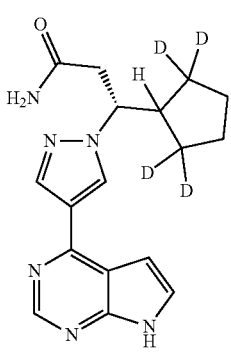

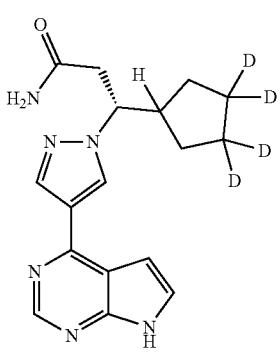

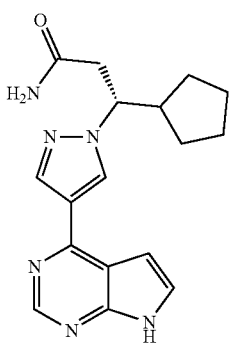

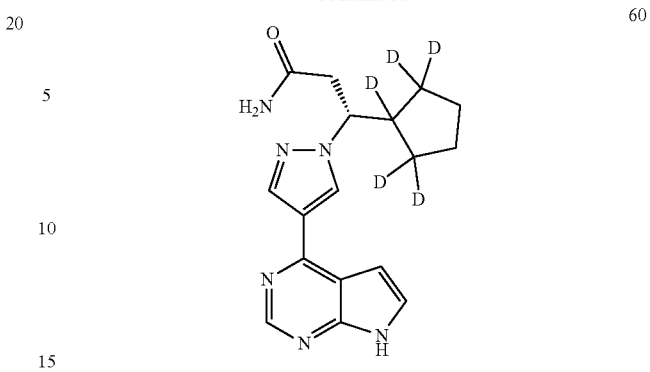

Certain aspects of the present invention are directed to pharmaceutical compositions comprising a compound of Formula (I), or a pharmaceutically acceptable salt thereof, and a pharmaceutically acceptable carrier. In some embodiments, the pharmaceutical composition comprises: (i) a compound of Formula (I), or a pharmaceutically acceptable salt thereof, (ii) one or more (e.g., 1, 2 or 3) additional JAK inhibitors (i.e., JAK inhibitors other than the compound of Formula (I)); and a pharmaceutically acceptable carrier.

Certain aspects of the present invention are directed to a method for treating hair loss disorders in a human subject, comprising administering a compound of Formula (I), or a pharmaceutically acceptable salt thereof, to a human subject in need of such treatment. In some embodiments, the hair loss disorder is alopecia areata. In some embodiments, the compound of Formula (I) is administered as a pharmaceutically acceptable salt, such as the phosphate salt.

Other aspects of the present invention are directed to a method for treating a disease or disorder in a human subject that is beneficially treated by inhibiting the activity of JAK, including hair loss disorders, in a human subject in need of such treatment, comprising administering to the human subject a combination of JAK inhibitors. The method comprises administering to the human subject a therapeutically effective amount of a pharmaceutical composition comprising (a) a first JAK inhibitor which is a compound of Formula (I) or a pharmaceutically acceptable salt thereof; (b) a second JAK inhibitor or a pharmaceutically acceptable salt thereof; and (iii) a pharmaceutically acceptable carrier.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

"Hair loss disorder" means any condition or disorder that results in loss of hair on one or more areas of the body. Hair loss disorders include, without limitation, androgenetic alopecia, telogen effluvium, alopecia areata, alopecia totalis, and alopecia universalis. In certain embodiments, for purposes of this application, alopecia areata includes all forms of alopecia, including patchy alopecia, alopecia totalis, alopecia universalis, and ophiasis.

The term "mammal", as used herein, includes humans, as well as non-human mammals such as cats, dogs, sheep, cattle, pigs, goats, non-human primates (including monkeys and apes) and the like.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

Unless otherwise stated, when a position in a compound of this invention is designated specifically as "H" or "hydrogen", the position is understood to have hydrogen at its natural abundance isotopic composition. However, in some embodiments, where specifically stated, when a position is designated specifically as "H" or "hydrogen", the position incorporates ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, in a compound of this invention, each designated deuterium atom has deuterium incorporation of at least 52.5%. In some embodiments, in a compound of this invention, each designated deuterium atom has deuterium incorporation of at least 60%. In some embodiments, in a compound of this invention, each designated deuterium atom has deuterium incorporation of at least 67.5%. In some embodiments, in a compound of this invention, each designated deuterium atom has deuterium incorporation of at least 75%. In some embodiments, in a compound of this invention, each designated deuterium atom has deuterium incorporation of at least 80%. In some embodiments, in a compound of this invention, each designated deuterium atom has deuterium incorporation of at least 85%. In some embodiments, in a compound of this invention, each designated deuterium atom has deuterium incorporation of at least 90%. In some embodiments, in a compound of this invention, each designated deuterium atom has deuterium incorporation of at least 95%. In some embodiments, in a compound of this invention, each designated deuterium atom has deuterium incorporation of at least 97%. In some embodiments, in a compound of this invention, each designated deuterium atom has deuterium incorporation of at least 98%. In some embodiments, in a compound of this invention, each designated deuterium atom has deuterium incorporation of at least 99%. In some embodiments, in a compound of this invention, each designated deuterium atom has deuterium incorporation of at least 99.5%.

The term "isotopologue" refers to a species in which the chemical structure differs from Formula (I) only in the isotopic composition thereof.

The term "compound," when referring to a compound of this invention, refers to a collection of molecules having an identical chemical structure, except that there may be isotopic variation among the constituent atoms of the molecules. Thus, it will be apparent to those of skill in the art that a compound represented by a particular chemical structure will contain molecules having deuterium at each of the positions designated as deuterium in the chemical structure, and may also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of compounds of Formula (I). A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt, such as a phosphate salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

Therapeutic Compounds

In certain aspects, the invention provides a compound of the following structural formula:

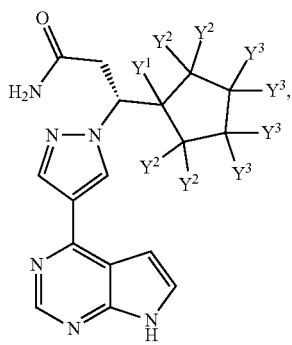

Formula (I)

or pharmaceutically acceptable salt thereof, wherein $Y^1$ is selected from hydrogen and deuterium; each $Y^2$ is selected from hydrogen and deuterium; and each $Y^3$ is selected from hydrogen and deuterium, and each $Y^3$ is the same. In some embodiments, each $Y^2$ is the same. In some embodiments, each $Y^3$ is the same. In some embodiments, at least one of $Y^1$, $Y^2$, and $Y^3$ is deuterium. In some embodiments, $Y^1$ is hydrogen. In some embodiments, when $Y^1$ is hydrogen, the position incorporates ≤2% deuterium, or ≤1% deuterium. In some embodiments, $Y^1$ is deuterium. In some embodiments, each $Y^2$ is hydrogen. In some embodiments, when $Y^2$ is hydrogen, the position incorporates ≤2% deuterium, or ≤1% deuterium. In some embodiments, each $Y^2$ is deuterium. In some embodiments, each $Y^3$ is hydrogen. In some embodiments, when $Y^3$ is hydrogen, the position incorporates ≤2% deuterium, or ≤1% deuterium. In some embodiments, each $Y^3$ is deuterium. In some embodiments, each $Y^2$ and each $Y^3$ is deuterium. In some embodiments, $Y^1$ is deuterium, and each $Y^2$ and each $Y^3$ is deuterium. Specific examples of a compound of Formula (I) include the following:

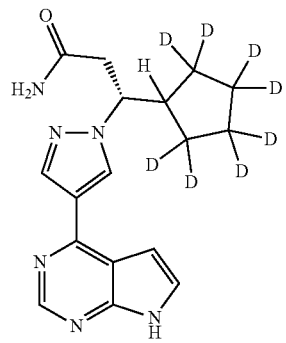

10

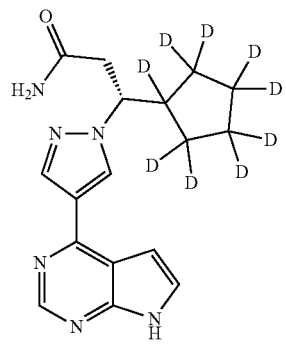

20

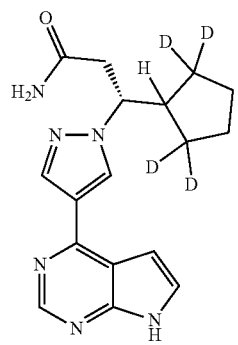

30

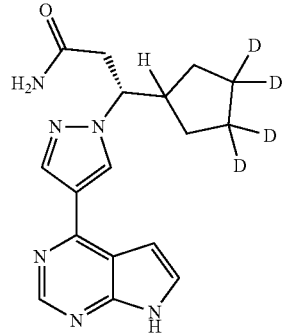

40

-continued

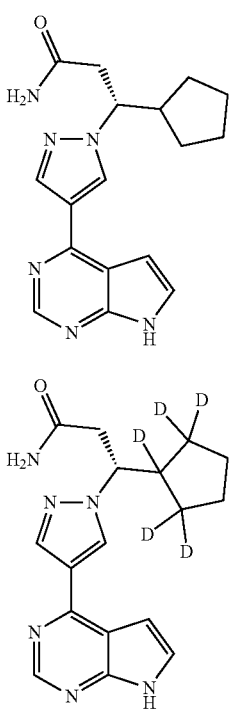

In some embodiments, the compound of Formula (I) is an isolated compound of at least 90% purity, or at least 95% purity, at least 97% purity, at least 98% purity, or at least 99% purity as measured by HPLC (e.g., Waters XBridge C18, 4.6×150 mm, 3.5 μm column (Waters, P/N 186003034); mobile phases composed of 10 mM ammonium formate, pH 3.9 in water and acetonitrile; under gradient elution conditions; flow rate of 1.0 mL/min; column temperature of 40° C.; detection by ultraviolet (UV) absorbance at 254 nm; retention time of approximately 11-12 minutes for compounds of Formula (I)).

In certain embodiments, the compound of Formula (I) is the (R)-enantiomer, substantially free of the (S)-enantiomer. Enantiomeric purity can be assessed by art-recognized methods such as chiral HPLC. In certain embodiments, the compound of Formula (I) is the (R)-enantiomer with an enantiomeric excess (e.e.) of at least 95% e.e., or at least 98% e.e., or at least 99% e.e.

In some embodiments, each position of a compound of Formula (I) designated specifically as deuterium has at least 90% deuterium incorporation, at least 95% deuterium incorporation, at least 97% deuterium incorporation, at least 98% deuterium incorporation, or at least 99% deuterium incorporation. In some embodiments, the pharmaceutically acceptable salt is a phosphate salt.

In one embodiment, any atom not designated as deuterium is present at its natural isotopic abundance in compounds of Formula (I), or a pharmaceutically acceptable salt thereof.

Compounds of Formula (I) can be prepared by a variety of methods. For example, a compound of Formula (I) can be prepared from CTP-543, e.g., as described in Example 1, infra.

Methods of preparing compounds of Formula (I) can also be carried out using any suitable method for the preparation of the corresponding non-deuterated compound, utilizing corresponding deuterated and optionally, other isotope-containing reagents and/or intermediates to synthesize the compounds delineated herein, or invoking standard synthetic protocols known in the art for introducing isotopic atoms to a chemical structure.

In another aspect, the invention provides a method of preparing a compound of Formula (I), or a salt thereof. The method comprises hydrolyzing a compound of Formula (II):

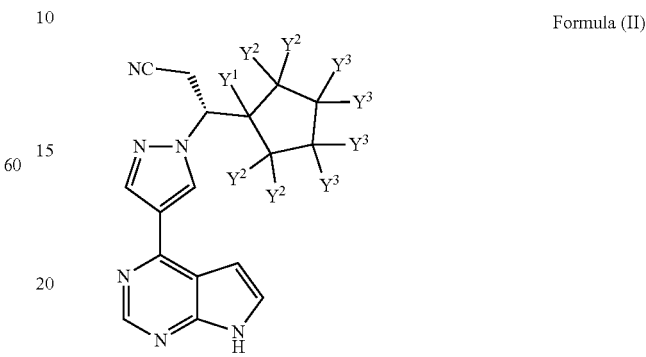

Formula (II)

or a salt thereof,
wherein $Y^1$ is selected from hydrogen and deuterium; each $Y^2$ is selected from hydrogen and deuterium; and each $Y^3$ is selected from hydrogen and deuterium, under hydrolytic conditions suitable for converting a nitrile group to an amide group, such that a compound of Formula (I) is prepared. In certain embodiments, each $Y^2$ is the same. In some embodiments, each $Y^3$ is the same. In some embodiments, at least one of $Y^1$, $Y^2$, and $Y^3$ is deuterium. In some embodiments, $Y^1$ is hydrogen. In some embodiments, $Y^1$ is deuterium. In some embodiments, each $Y^2$ is hydrogen. In some embodiments, each $Y^2$ is deuterium. In some embodiments, each $Y^3$ is hydrogen. In some embodiments, each $Y^3$ is deuterium. In some embodiments, each $Y^2$ and each $Y^3$ is deuterium. In some embodiments, $Y^1$ is deuterium, and each $Y^2$ and each $Y^3$ is deuterium. Exemplary compounds of Formula (II) include ruxolitinib and CTP-543. The method optionally includes the further step of forming a salt of the compound of Formula (I). Hydrolytic conditions include contact with an acid, such as sulfuric acid, for a time sufficient to produce a compound of Formula (I) (e.g., from about 2 hours to about 6 hours, such as 4 hours). The method optionally includes the further step of neutralizing the acid with a base, such as sodium or potassium carbonate.

As used herein, "hydrolysis reaction" or "hydrolyzing" means a chemical reaction in which a substance or functional group reacts with water so as to be changed into one or more other substances_or functional groups. For example as described herein, a nitrile group can be converted to an amide group by acid-catalyzed hydrolysis of the nitrile group.

Pharmaceutical Compositions

In certain aspects, the invention also provides pharmaceutical compositions comprising a compound of Formula (I), or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament. In certain embodiments, the pharmaceutical composition is provided as a unit dose form.

In certain aspects, the invention provides a pharmaceutical composition comprising a pharmaceutically acceptable carrier and a compound represented by the following structural formula:

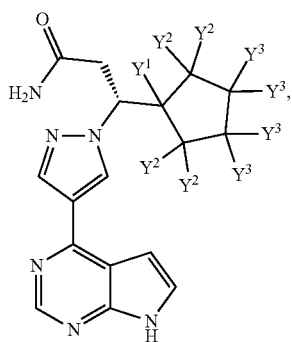

Formula (I)

or a pharmaceutically acceptable salt thereof, wherein $Y^1$ is selected from hydrogen and deuterium; each $Y^2$ is selected from hydrogen and deuterium; and each $Y^3$ is selected from hydrogen and deuterium. In some embodiments, each $Y^2$ is the same. In some embodiments, each $Y^3$ is the same. In some embodiments, at least one of $Y^1$, $Y^2$, and $Y^3$ is deuterium. In some embodiments, $Y^1$ is hydrogen. In some embodiments, when $Y^1$ is hydrogen, the position incorporates ≤2% deuterium, or ≤1% deuterium. In some embodiments, $Y^1$ is deuterium. In some embodiments, each $Y^2$ is hydrogen. In some embodiments, when $Y^2$ is hydrogen, the position incorporates ≤2% deuterium, or ≤1% deuterium. In some embodiments, each $Y^2$ is deuterium. In some embodiments, each $Y^3$ is hydrogen. In some embodiments, when $Y^3$ is hydrogen, the position incorporates ≤2% deuterium, or ≤1% deuterium. In some embodiments, each $Y^3$ is deuterium. In some embodiments, each $Y^2$ and each $Y^3$ is deuterium. In some embodiments, $Y^1$ is deuterium, and each $Y^2$ and each $Y^3$ is deuterium. Specific examples of a compound of Formula (I) include the following:

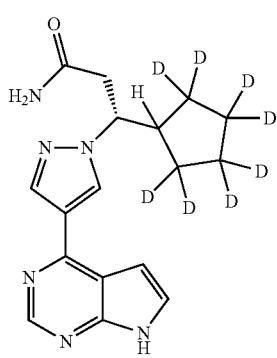

10

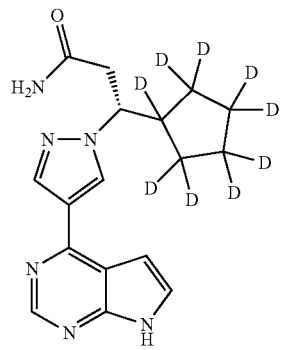

20

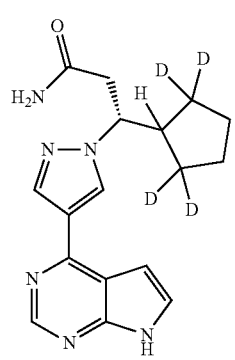

30

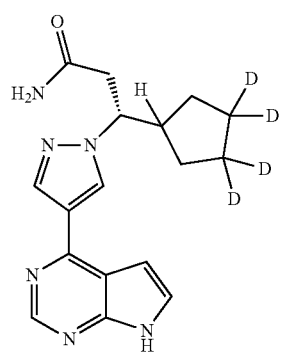

40

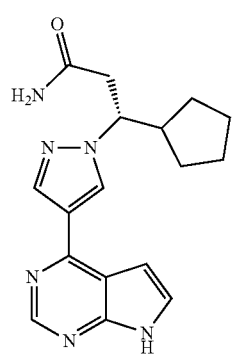

50

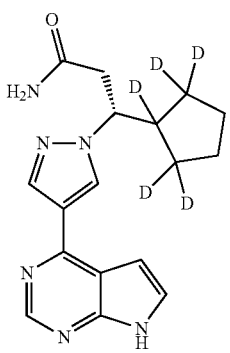

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral administration. Other formulations may conveniently be presented in unit dosage form, e.g., tablets, sustained release capsules, granules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In a specific embodiment, the compound is administered orally as a tablet.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. In another embodiment, the composition is in the form of a tablet. In certain embodiments, exemplary formulations for the tablet are disclosed in U.S. Pat. No. 8,754,224, the teachings of which are herein incorporated by reference.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

In another embodiment, a pharmaceutical composition of this invention comprises (i) a compound of Formula (I), or a pharmaceutically acceptable salt thereof (ii) one or more (e.g., 1, 2 or 3) additional therapeutic agents; and (iii) a pharmaceutically acceptable carrier. The additional therapeutic agent may be selected from any compound or therapeutic agent known to have or that demonstrates advantageous properties when administered with a compound having the same mechanism of action as that of a compound of Formula (I).

Preferably, the additional therapeutic agent is an agent useful in the treatment of JAK1 and/or JAK2-mediated diseases and conditions, including inflammatory and/or autoimmune conditions (including hair loss disorders such as alopecia areata), including JAK inhibitors other than the compound of Formula (I). Such JAK inhibitors include CTP-543, ruxolitinib, tofacitinib, baricitinib, upadacitinib, fedratinib, filgotinib, momelotinib, pacritinib, itacitinib, peficitinib, PF-06700841 (brepocitinib), and abrocitinib, and pharmaceutically acceptable salts thereof. Other additional therapeutic agents include oral or topical corticosteroids. In some embodiments, the additional therapeutic agent is CTP-543 or a pharmaceutically acceptable salt thereof (e.g., a phosphate salt).

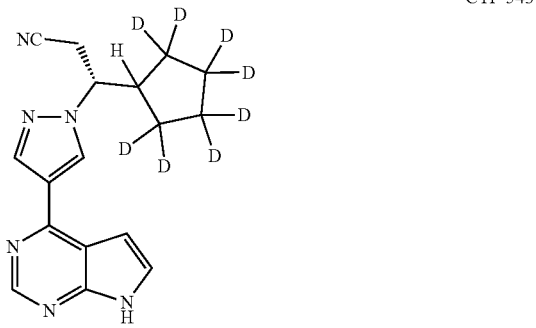

CTP-543

In certain embodiments, the pharmaceutical composition comprises (i) a compound of Formula (I), or a pharmaceutically acceptable salt thereof; (ii) CTP-543, or a pharmaceutically acceptable salt thereof; and (iii) a pharmaceutically acceptable carrier. In certain embodiments, the amount of CTP-543 is 8 mg, 12 mg, 16 mg, or 24 mg.

In some embodiments, a compound of Formula (I), or a pharmaceutically acceptable salt thereof, and one or more of any of the above-described additional therapeutic agents are combined in a single dosage form. In another embodiment, the invention provides separate dosage forms of a compound of Formula (I), or a pharmaceutically acceptable salt thereof, and one or more of any of the above-described additional therapeutic agents, wherein the compound of Formula (I), or a pharmaceutically acceptable salt thereof, and additional therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In some embodiments of the pharmaceutical compositions of the invention, a compound of Formula (I), or a pharmaceutically acceptable salt thereof, is present in an effective amount. As used herein, the term "effective amount" or "therapeutic effective amount" refers to an amount which, when administered in a proper dosing regimen, is sufficient to treat the target disorder.

An effective amount can be achieved in the methods or compositions of the invention by administering a therapeutically effective amount of a composition comprising a compound of Formula (I) or a pharmaceutically acceptable salt thereof, and a second JAK inhibitor (i.e., a JAK inhibitor other than the compound of Formula (I)). Such a composition may comprise an amount wherein at least one of the JAK inhibitors would not be therapeutic if administered without the other JAK inhibitor. The relative amounts of each JAK inhibitor necessary to provide a therapeutically effective amount of a composition containing more than one JAK inhibitor may be determined by one skilled in the art by reference to the relative potencies and other known properties of the two drugs.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of Formula (I) can range from 50 mg to 1000 mg per day, such as, about 100 mg to about 1000 mg per day, about 200 mg to about 800 mg per day, about 200 mg to about 400 mg per day, about 400 mg to about 600 mg per day, or about 600 mg to about 800 mg per day. It will be understood that reference to an amount of a compound of Formula (I), or a pharmaceutically acceptable salt thereof, includes an amount of a pharmaceutically acceptable salt of the compound of Formula (I) (such as the phosphate salt) which is equivalent to the stated amount of the compound of Formula (I) as the free base. For example, about 20.7 mg of Compound 10 phosphate salt is equivalent to 16 mg of Compound 10 free base).

In some embodiments, the pharmaceutical composition comprises an effective amount of a composition comprising (i) a first JAK inhibitor which is a compound of Formula (I), or a pharmaceutically acceptable salt thereof; (ii) an additional therapeutic agent; and a pharmaceutically acceptable carrier. In some embodiments, the pharmaceutical composition comprises: (i) a compound of Formula (I) or a pharmaceutically acceptable salt thereof; (ii) one or more additional JAK inhibitors (i.e., a JAK inhibitor other than the compound of Formula (I); and a pharmaceutically acceptable carrier. Examples of JAK inhibitors include, but are not limited to, CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib, and pharmaceutically acceptable salts thereof. In some embodiments, the JAK inhibitor is CTP-543, or a pharmaceutically acceptable salt thereof. In some embodiments, the composition comprises about 8 mg, 12 mg, 16 mg, 24 mg, or 32 mg of the first JAK inhibitor and the second JAK inhibitor together.

In another embodiment, the invention provides a unit dose form comprising a compound of Formula (I), or a pharmaceutically acceptable salt thereof and a pharmaceutically acceptable carrier. In certain embodiments, the unit dose form comprises a compound of Formula (I), or a pharmaceutically acceptable salt thereof, together with an additional therapeutic agent, such as an additional JAK inhibitor; and a pharmaceutically acceptable carrier. In certain embodiments, the additional therapeutic agent is CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib, or a pharmaceutically acceptable salt thereof. In certain embodiments, the additional therapeutic agent is CTP-543, or a pharmaceutically acceptable salt thereof. In certain embodiments, the amount of CTP-543, or a pharmaceutically acceptable salt thereof, in the unit dose form is about 8 mg, 12 mg, 16 mg, or 24 mg. In certain embodiments, the amount of CTP-543, or a pharmaceutically acceptable salt thereof, in the unit dose form is about 8 mg or about 12 mg. In certain embodiments, the amount of CTP-543, or a pharmaceutically acceptable salt thereof, in the unit dose form is about 16 mg or about 24 mg. In certain embodiments, the amount of the compound of Formula (I), or a pharmaceutically acceptable salt thereof, is between 1 mg and 50 mg. In certain embodiments, the unit dose form is a tablet. In certain embodiments, the unit dose form is a capsule.

Methods of Treatment

In another aspect, the invention provides a method of modulating the activity of JAK1 and/or JAK2 in a cell, comprising contacting a cell with a compound of Formula (I) herein, or a pharmaceutically acceptable salt thereof. In some embodiments, the cell is contacted in vitro. In some embodiments, the cell is contacted in vivo. In some embodiments, the cell is contacted ex vivo. In certain embodiments, the method comprises contacting the cell with a compound of Formula (I) or a pharmaceutically acceptable salt thereof, and one or more additional JAK inhibitors selected from CTP-543, ruxolitinib, tofacitinib, baricitinib, upadacitinib, fedratinib, filgotinib, momelotinib, pacritinib, itacitinib, peficitinib, PF-06700841 (brepocitinib), PF-06651600, and abrocitinib or pharmaceutically acceptable salts thereof.

In certain aspects, the invention provides a method of treating a disease or disorder that is beneficially treated by compounds that modulate (e.g., inhibit) the activity of a JAK (JAK1, JAK2 and/or JAK3) in a subject in need thereof, comprising the step of administering to the subject a pharmaceutical composition comprising a compound of Formula (I) or a pharmaceutically acceptable salt thereof. In one embodiment the subject is a patient in need of such treatment. Such diseases include, but are not limited to, diseases involving the immune system including, for example, organ transplant rejection (e.g., allograft rejection and graft versus host disease); autoimmune diseases such as hair loss disorders (e.g., alopecia areata, alopecia totalis, alopecia universalis, and ophiasis), atopic dermatitis, vitiligo, multiple sclerosis, rheumatoid arthritis, juvenile arthritis, psoriatic arthritis, ankylosing spondylitis, axial spondyloarthritis, primary biliary cholangitis, type I diabetes, lupus, psoriasis, inflammatory bowel disease, ulcerative colitis, Crohn's disease, myasthenia gravis, immunoglobulin nephropathies, autoimmune thyroid disorders, giant cell arteritis, Takayasu's arteritis, uveitis, Sjogren syndrome; allergic conditions such as asthma, food allergies, atopic dermatitis and rhinitis; viral diseases such as Epstein Barr virus (EBV), hepatitis B, hepatitis C, HIV, HTLV 1, varicella-zoster virus (VZV) and human papilloma virus (HPV); skin disorders such as psoriasis (for example, psoriasis vulgaris), atopic dermatitis, skin rash, skin irritation, skin sensitization (e.g., contact dermatitis or allergic contact dermatitis; cancer, including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma), hematological cancers (e.g., lymphoma, leukemia such as acute lymphocytic leukemia, chronic lymphocytic leukemia, non-Hodgkin's lymphoma, or multiple myeloma), and skin cancer such as cutaneous T-cell lymphoma (CTCL) and cutaneous B-cell lymphoma (examples of which include Sezary syndrome and mycosis fungoides; myeloproliferative disorders (MPDs) such as myelofibrosis, polycythemia vera (PV), essential thrombocythemia (ET), myeloid metaplasia with myelofibrosis (MMM), chronic myelomonocytic leukemia (CMML), hypereosinophilic syndrome (HES), systemic mast cell disease (SMCD); inflammation and inflammatory diseases, such as inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis; systemic inflammatory response syndrome (SIRS) and septic shock; ischemia reperfusion injuries or a disease or condition related to an inflammatory ischemic event such as stroke or cardiac arrest; anorexia; cachexia; fatigue such as that resulting from or associated with cancer; restenosis; sclerodermitis; fibrosis; conditions associated with hypoxia or astrogliosis such as, for example diabetic retinopathy, cancer or neurodegeneration; gout; increased prostate size due to, e.g., benign prostatic hypertrophy or benign prostatic hyperplasia.

In certain aspects, the invention provides a method for treating hair loss disorders that can be treated by compounds that modulate (e.g., inhibit) the activity of a JAK (JAK1, JAK2 and/or JAK3). The method comprises administering to a mammalian (e.g., human) subject a pharmaceutical composition comprising a compound of Formula (I), or a pharmaceutically acceptable salt thereof.

In certain embodiments, a compound of Formula (I), or a pharmaceutically acceptable salt thereof, is administered in the range of about 50 mg to about 1000 mg per day, about 100 mg to about 1000 mg per day, about 200 mg to about 800 mg per day, about 200 mg to about 400 mg per day, about 400 mg to about 600 mg per day, or about 600 mg to about 800 mg per day. In certain embodiments, a compound of Formula (I), or a pharmaceutically acceptable salt thereof, is dosed at about 50 mg/day, about 100 mg/day, about 200 mg/day, about 400 mg/day, 500 mg/day about 600 mg/day, about 700 mg/day, about 800 mg/day, about 900 mg/day, or about 1000 mg/day.

In some embodiments, the method for treating hair loss disorders comprises administering a therapeutically effective amount of a composition comprising (i) a first JAK inhibitor which is a compound of Formula (I) or a pharmaceutically acceptable salt thereof; and (ii) a second JAK inhibitor. In some embodiments, the composition is a pharmaceutical composition which further comprises (iii) a pharmaceutically acceptable carrier. Examples of second JAK inhibitors include, but are not limited to, CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib, and pharmaceutically acceptable salts thereof. In some embodiments, the second JAK inhibitor is CTP-543, or a pharmaceutically acceptable salt thereof. In another embodiment the first JAK inhibitor is Compound 10 and the second JAK inhibitor is CTP-543. In some embodiments, the amount of the first JAK inhibitor and the second JAK inhibitor together is 12 mg/day, 16 mg/day, 24 mg/day, 32 mg/day, or 48 mg/day. In some embodiments, the composition is administered at 16 mg/day or 24 mg/day of the first JAK inhibitor and the second JAK inhibitor together. In some embodiments, the method comprises administering the first JAK inhibitor and the second JAK inhibitor together at 8 mg once a day, 8 mg twice a day, 12 mg once a day, 12 mg twice a day, 16 mg once a day, 16 mg twice a day, 24 mg once a day, or 24 mg twice a day. In some embodiments, the method comprises administering the first JAK inhibitor and the second JAK inhibitor together at 8 mg twice a day or 12 mg twice a day.

Hair loss disorders include, without limitation, androgenetic alopecia, alopecia areata, ophiasis, telogen effluvium, alopecia totalis, and alopecia universalis. The term alopecia areata can include alopecia totalis and alopecia universalis.

Alopecia areata is an autoimmune disease that results in partial or complete loss of hair on the scalp and body that may affect up to 650,000 Americans at any given time. The scalp is the most commonly affected area, but any hair-bearing site can be affected alone or together with the scalp. Onset of the disease can occur throughout life and affects both women and men. Alopecia areata can be associated with serious psychological consequences, including anxiety and depression. There are currently no drugs approved by the U.S. Food and Drug Administration (FDA) for the treatment of alopecia areata.

In a specific embodiment, the condition is alopecia areata in a subject such as a mammalian (e.g., human) patient in need thereof. In certain embodiments, the alopecia areata is moderate to severe alopecia areata (for example, hair loss over at least 30% of the scalp, hair loss over at least 40% of the scalp, or hair loss over at least 50% of the scalp).

In one embodiment, the compound is used to treat loss of facial hair, including eyebrows, eyelashes, nose hair, mustache, and/or beard.

In another embodiment, the compound is used to treat other manifestations of alopecia areata, including scalp pain or sensitivity, or malformed fingernails or toenails.

In one embodiment of any aspect, the compound is administered orally once a day. In other embodiments of any aspect, the compound is administered orally twice per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

The administration of a compound of Formula (I), or a pharmaceutically acceptable salt thereof (such as the phosphate salt), can continue for as long as necessary to treat a hair loss disorder, e.g., for one week, two weeks, one month, two months, three months, four months, six months, one year, two years, five years, ten years, or longer.

The efficacy of treatment of hair loss disorders such as alopecia areata can be measured in a variety of ways, some of which are known in the art. For example, the "severity of alopecia tool", otherwise known as SALT, is a validated assessment scale—developed by the National Alopecia Areata Foundation working committee—to evaluate the degree of hair loss. See, e.g., Olsen E A, Hordinsky M K, Price V H, et al. Alopecia areata investigational assessment guidelines—Part II. J Am Acad Dermatol 2004: 51: 440-447 (incorporated herein by reference). The SALT score is calculated for a patient by measuring the percentage of hair loss in each of the 4 areas of the scalp and adding the total to achieve a composite score. Hair regrowth is reflected by a decrease in the SALT score. For example, no hair on the scalp would have a SALT score of 100 while complete hair regrowth would be a SALT score of 0. In certain embodiments, methods of treatment as described herein can provide a SALT score improvement of at least 10 points after treatment (for example, from a SALT score of 100 prior to treatment to a SALT score of 90 after treatment). In further embodiments, methods of treatment as described herein can provide a SALT score improvement of at least 20 points, 30 points, 40 points, 50 points, 60 points, 70 points, 80 points, 90 points, or 100 points. In certain embodiments, methods of treatment as described herein can provide after treatment at least a 20% improvement from baseline in the patient's SALT score, or at least a 30% improvement from baseline in the patient's SALT score, or at least a 40% improvement from baseline in the patient's SALT score, or at least a 50% improvement from baseline in the patient's SALT score, or at least a 60% improvement from baseline in the patient's SALT score, or at least a 70% improvement from baseline in the patient's SALT score.

In certain embodiments, treatment is continued for a period of at least four weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In certain embodiments, a compound of Formula (I), or a pharmaceutically acceptable salt thereof, is administered with CTP-543 or a pharmaceutically acceptable salt thereof (e.g., a phosphate salt):

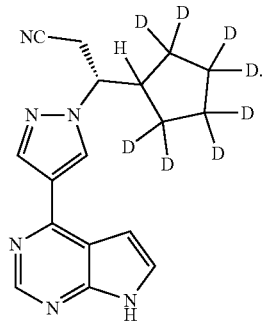

CTP-543

For pharmaceutical compositions that comprise one or more additional therapeutic agents, an effective amount of the additional therapeutic agent may be at or near its normal monotherapeutic dose. The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); the FDA-approved labeling information for ruxolitinib and tofacitinib; and clinical trial information for CTP-543, baricitinib and filgotinib, each of which references are incorporated herein by reference in their entirety. The normal monotherapeutic dosages for CTP-543 include 16 mg/day and 24 mg/day, e.g., 8 mg twice a day, 12 mg twice a day, 16 mg once a day, and 24 mg once a day.

Some of the additional therapeutic agents referenced above may act synergistically with the compounds of this invention. When this occurs, it will allow the effective dosage of the additional therapeutic agent and/or a compound of Formula (I), or a pharmaceutically acceptable salt thereof, to be reduced from that required in a monotherapy. This has the advantage of minimizing toxic side effects of either the additional therapeutic agent or the compound of Formula (I), or a pharmaceutically acceptable salt thereof, synergistic improvements in efficacy, improved ease of administration or use and/or reduced overall expense of compound preparation or formulation.

The choice of additional therapeutic agent is dependent upon the particular disease or condition to be treated. For the treatment of hair loss, the choice of additional therapeutic agent may be made from any additional therapeutic agent known to be useful for treatment of hair loss disorders such as alopecia areata. Examples of additional therapeutic agents that may be employed in the methods of this invention are those set forth above for use in combination compositions comprising a compound of Formula (I), or a pharmaceutically acceptable salt thereof, and an additional therapeutic agent. Additional therapeutic agents include agents used in the treatment of alopecia areata, including, for example, topical minoxidil, injected corticosteroids, and anthralin cream or ointment.

The term "co-administered" as used herein means that the additional therapeutic agent may be administered together with a compound of Formula (I) or a pharmaceutically acceptable salt thereof, as part of a single dosage form (such as a pharmaceutical composition of this invention comprising the compound of Formula (I), or a pharmaceutically acceptable salt thereof, and an additional therapeutic agent as described above) or as separate, multiple dosage forms. Alternatively, the additional agent may be administered prior to, consecutively with, or following the administration of a compound of Formula (I), or a pharmaceutically acceptable salt thereof. In such combination therapy treatment, both the compound of Formula (I), or a pharmaceutically acceptable salt thereof, and the additional therapeutic agent(s) are administered by conventional methods. The administration of a pharmaceutical composition of this invention, comprising both a compound of Formula (I), or a pharmaceutically acceptable salt thereof, and an additional therapeutic agent, to a subject does not preclude the separate administration of that same therapeutic agent, any other additional therapeutic agent or a compound of Formula (I), or a pharmaceutically acceptable salt thereof, to said subject at another time during a course of treatment.

In one embodiment of the invention, where an additional therapeutic agent is administered to a subject, the effective amount of a compound of Formula (I), or a pharmaceutically acceptable salt thereof, is less than its effective amount would be where the additional therapeutic agent is not administered. In another embodiment, the effective amount of the additional therapeutic agent is less than its effective amount would be where a compound of Formula (I), or a pharmaceutically acceptable salt thereof, is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula (I), or a pharmaceutically acceptable salt thereof, alone or together with one or more of the above-described additional therapeutic agents in the manufacture of a medicament, either as a single composition or as separate dosage forms, for treatment or prevention in a subject of a disease, disorder or symptom set forth above. Another aspect of the invention is a compound of Formula (I), or a pharmaceutically acceptable salt thereof, for use in the treatment or prevention in a subject of a disease, disorder or symptom thereof delineated herein.

EXAMPLES

Example 1

Synthesis of Compound 10

The synthesis of Compound 10, or a pharmaceutically acceptable salt thereof (such as the phosphate salt) may be readily achieved, e.g., reaction of CTP-543 under conditions suitable to provide hydrolysis of the nitrile functionality of CTP-543. CTP-543 can be prepared, e.g., according to the methods described in U.S. Pat. No. 9,249,149 and US Patent Pub. No. 2019/0160068 (the teachings of which are incorporated herein by reference), to produce CTP-543 and/or its phosphate salt. CTP-543 phosphate salt may be transformed into Compound 10 or its phosphate salt according to Scheme 1 below.

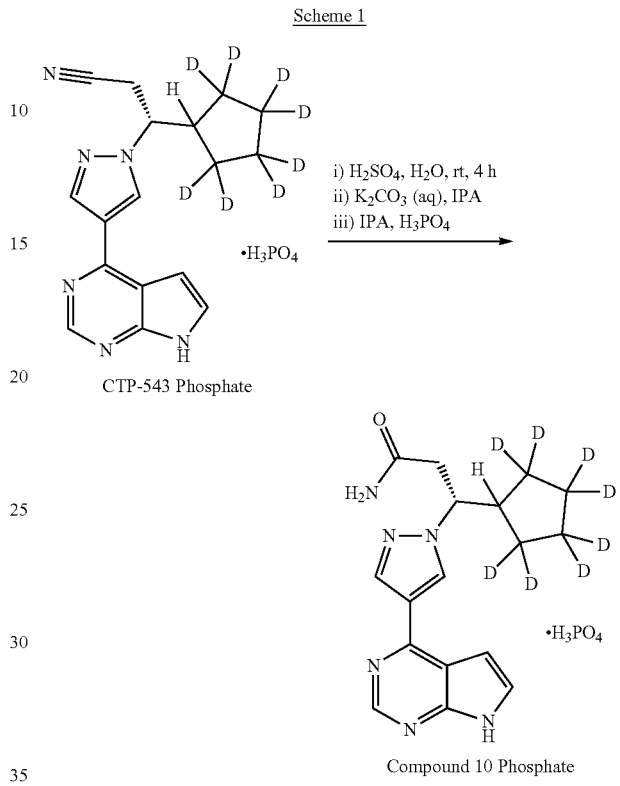

To a round bottom flask, equipped with a magnetic stir bar, was charged sulfuric acid (2 mL) followed by careful addition of CTP-543 Phosphate (4.05 g, 9.8 mmol). To the mixture was added another portion of sulfuric acid (2 mL) and water (0.8 mL). The reaction was stirred at room temperature for 4 hours, then quenched by addition of a potassium carbonate solution (80 g, 30% w/w). The product was extracted using isopropyl alcohol. The organic phase was concentrated under vacuum to dryness. The product was dissolved in isopropyl alcohol (100 mL) and phosphoric acid (1 mL, 85% w/w) was added to crystallize the product as the phosphate salt. The precipitate was filtered and dried in a vacuum oven (5 torr, room temp, slight nitrogen purge) to yield the desired compound as an off-white solid (1.82 g, 4.2 mmol, 43% yield). The product was analyzed by HPLC, HRMS, and NMR.

$^1$H-NMR (400 MHz, DMSO-$d_6$): δ 12.05 (s, 1H), 8.64 (s, 1H), 8.56 (d, J=0.9 Hz, 1H), 8.26 (s, 1H), 7.55 (dd, J=3.6, 2.3 Hz, 1H), 7.33 (s, 1H), 6.96 (dd, J=3.6, 1.6 Hz, 1H), 6.76 (s, 1H), 4.57 (td, J=9.7, 4.0 Hz, 1H), 2.88 (dd, J=15.3, 10.0 Hz, 1H), 2.64 (dd, J=15.3, 4.0 Hz, 1H), 2.32 (d, J=9.3 Hz, 1H).

HPLC method summary: column=Waters XBridge C18, 4.6×150 mm, 3.5 μm column; gradient elution: mobile phase A=10 mM ammonium formate, pH 3.9; mobile phase B=acetonitrile; detection=ultraviolet absorbance at 254 nm. Result: Compound (I)=98.7 area %; retention time=11.1 min.

HRMS: Agilent 6530 Q-TOF LC/MS system with electrospray ionization in positive mode. The measured time-of-flight mass-to-charge ratio (m/z) is 333.22839 (theoretical value=333.22735).

Example 2

JAK Enzyme Functional Activity of Compound 10

JAK enzyme biochemical assays were performed at Eurofins CEREP, France using the kinase domains of human recombinant JAK1, JAK2, JAK3 and TYK2. Each enzyme reaction was carried out with Compound 10 (supplied by Concert Pharmaceuticals) or control, JAK enzyme, 100 nM substrate peptide (LANCE® Ultra U-light JAK-1 peptide) and adenosine triphosphate (ATP; concentration at $K_m$) for 60 minutes. Test compounds were dissolved in DMSO and tested in duplicate. Resulting $IC_{50}$'s for each enzyme are shown in Table 1 below. It can be seen that Compound 10 had significant potency for inhibition of JAK enzymes. Compound 10 was found to be a more potent inhibitor of JAK1 and JAK2 than JAK3 and Tyk2.

TABLE 1

| $IC_{50}$ (nM) | JAK1 | JAK2 | JAK3 | Tyk2 |
|---|---|---|---|---|
| Compound 10 | 63.90 | 34.00 | 226.00 | 368.00 |

Example 3

Determination of Metabolic Stability of Compound 10 Using Human Liver Microsomes Materials: Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich. Compound 10 and non-deuterated Compound 50 as test compounds were supplied by Concert Pharmaceuticals:

Compound 10

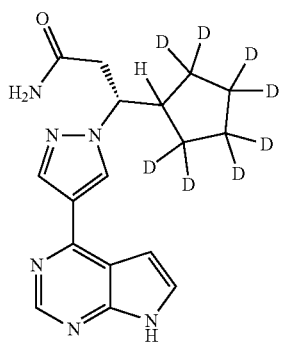

Compound 50

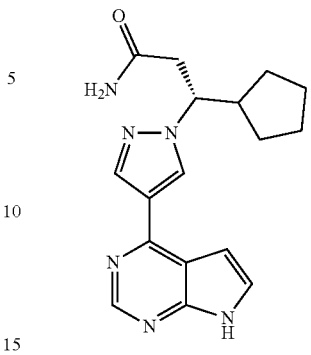

Determination of Metabolic Stability: 7.5 mM stock solutions of test compounds were prepared in DMSO. The 7.5 mM stock solutions were diluted to 12.5 µM in acetonitrile (ACN). The human liver microsomes were diluted in 0.1 M potassium phosphate buffer, pH 7.4, containing 3 mM $MgCl_2$. The diluted microsomes were added to wells of a 96-well deep-well polypropylene plate in triplicate. A 10 µL aliquot of the 12.5 µM test compound was added to the microsomes and the mixture was pre-warmed for 10 minutes. Reactions were initiated by addition of pre-warmed NADPH solution. The final reaction volume was 0.5 mL and contained 5 mg/mL human liver microsomes, 0.25 µM test compound, and 2 mM NADPH in 0.1 M potassium phosphate buffer, pH 7.4, and 3 mM $MgCl_2$. The reaction mixtures were incubated at 37° C., and 50 µL aliquots were removed at 0, 10, 20, 30, 45, and 60 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems mass spectrometer.

Data analysis: The in vitro $t_{1/2}$s for test compounds were calculated from the slopes of the linear regression of % parent remaining (ln) vs incubation time relationship.

in vitro $t_{1/2}=0.693/k$ $k=$−[slope of linear regression of % parent remaining(ln) vs incubation time]

Data analysis was performed using Microsoft Excel Software.

As shown in Table 2 below, Compound 10 was found to have an average 176% longer half-life ($t_{1/2}$) than the half-life of non-deuterated Compound 50. These results show that Compound 10 is substantially more stable metabolically than its non-deuterated analog Compound 50 in the HLM assay.

TABLE 2

| | $t_{1/2}$ (min) | | | |
|---|---|---|---|---|
| Compound ID | EXP# 2498 | EXP# 2500 | EXP# 2501 | Average % diff. |
| Compound 50 | 49.3 | 79.6 | 112 | 80 |
| Compound 10 | 96.0 | 270 | 298 | 221 176% |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound represented by the following structural formula:

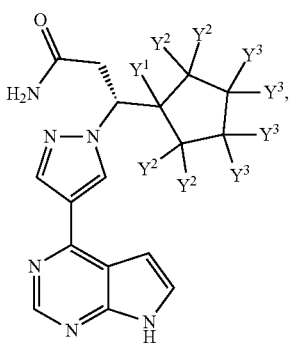

Formula (I)

or a pharmaceutically acceptable salt thereof, wherein
$Y^1$ is selected from hydrogen and deuterium;
each $Y^2$ is selected from hydrogen and deuterium; and
each $Y^3$ is selected from hydrogen and deuterium;
provided that at least one of $Y^1$, $Y^2$, and $Y^3$ is deuterium; and
wherein each position designated specifically as deuterium has at least 90% deuterium incorporation.

2. The compound of claim 1, selected from:

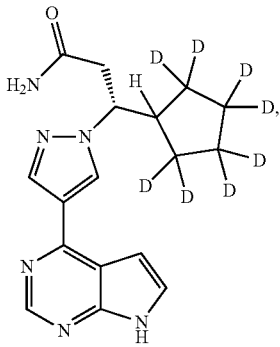

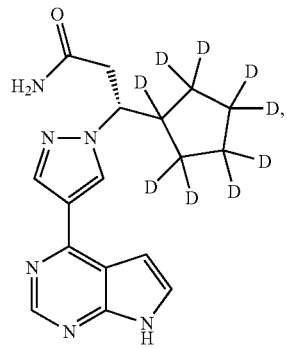

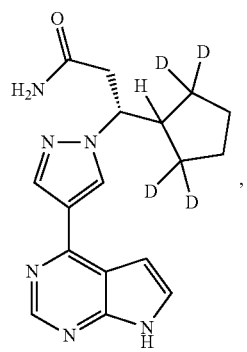

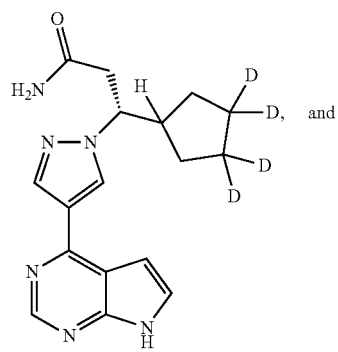

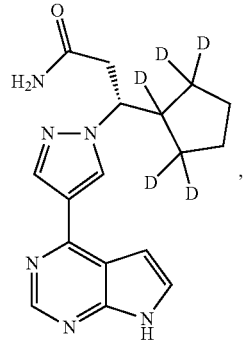

or a pharmaceutically acceptable salt thereof.

3. The compound of claim 2, which is Compound 10:

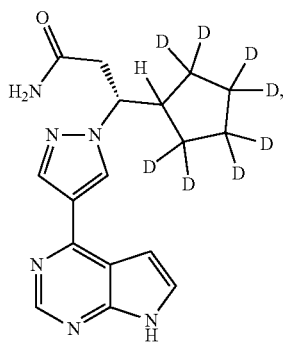

or a pharmaceutically acceptable salt thereof.

4. The compound of claim 1, wherein each position designated specifically as deuterium has at least 95% deuterium incorporation.

5. The compound of claim 1, wherein each position designated specifically as deuterium has at least 97% deuterium incorporation.

6. The compound of claim 1, wherein the pharmaceutically acceptable salt is a phosphate salt.

7. A pharmaceutical composition comprising a compound represented by the following structural formula:

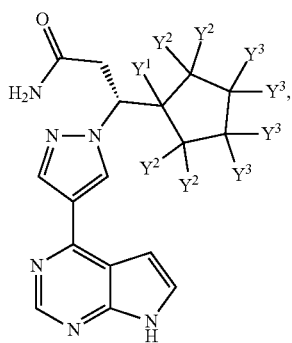

Formula (I)

or a pharmaceutically acceptable salt thereof, wherein $Y^1$ is selected from hydrogen and deuterium;

each $Y^2$ is selected from hydrogen and deuterium;

each $Y^3$ is selected from hydrogen and deuterium; and wherein each position designated specifically as deuterium has at least 90% deuterium incorporation; and a pharmaceutically acceptable carrier.

8. The pharmaceutical composition of claim 7, further comprising an additional therapeutic agent which is a JAK inhibitor.

9. The pharmaceutical composition of claim 8, wherein the additional therapeutic agent which is a JAK inhibitor is selected from CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib, or a pharmaceutically acceptable salt thereof.

10. The pharmaceutical composition of claim 9, wherein the compound of Formula (I) is

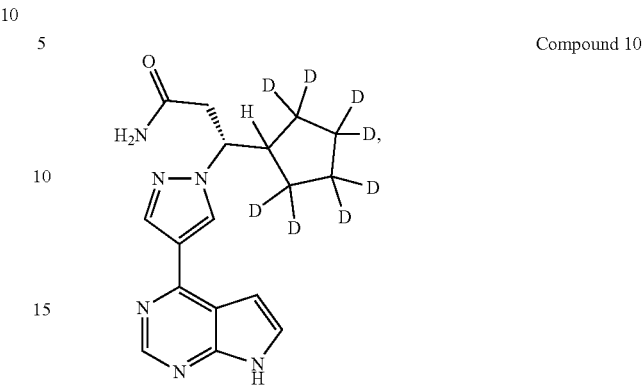

Compound 10 or a pharmaceutically acceptable salt thereof, and the JAK inhibitor is CTP-543, or a pharmaceutically acceptable salt thereof.

11. The pharmaceutical composition of claim 7, wherein the pharmaceutical formulation is in tablet form.

12. The pharmaceutical composition of claim 7, wherein the pharmaceutical formulation is in capsule form.

13. A method of inhibiting the activity of one or more of JAK1 or JAK2 in a cell, comprising contacting the cell with a compound of claim 1, or a pharmaceutically acceptable salt thereof.

14. The method of claim 13, further comprising contacting the cell with one or more additional JAK inhibitors selected from CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib; or a pharmaceutically acceptable salt thereof.

15. A method of treating a disease or disorder in a human subject that is beneficially treated by inhibiting the activity of a JAK, the method comprising administering to the subject an effective amount of a pharmaceutical composition comprising a compound represented by the following structural formula:

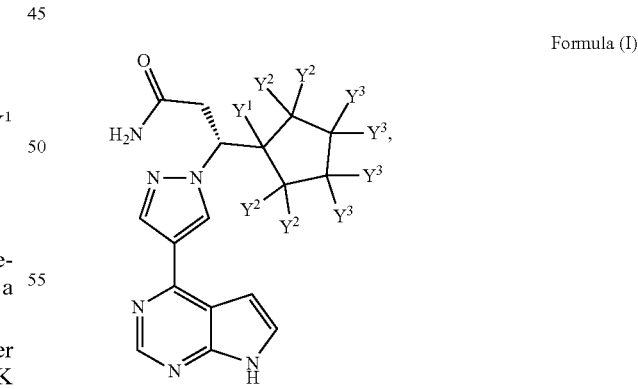

Formula (I)

or a pharmaceutically acceptable salt thereof, wherein $Y^1$ is selected from hydrogen and deuterium;

each $Y^2$ is selected from hydrogen and deuterium; and each $Y^3$ is selected from hydrogen and deuterium wherein each position designated specifically as deuterium has at least 90% deuterium incorporation;

and a pharmaceutically acceptable carrier.

16. The method of claim 15, wherein the disease or disorder is a hair loss disorder selected from alopecia areata, alopecia totalis, alopecia universalis, ophiasis, androgenic alopecia, and telogen effluvium.

17. The method of claim 16, wherein the hair loss disorder is alopecia areata.

18. The method of claim 15, wherein the pharmaceutically acceptable salt is a phosphate salt.

19. A method of treating a disease or disorder that is beneficially treated by inhibiting the activity of a JAK in a human subject in need thereof, comprising administering to the human subject an effective amount of a pharmaceutical composition comprising: (i) a first JAK inhibitor which is a compound represented by structural Formula (I)

Formula (I)

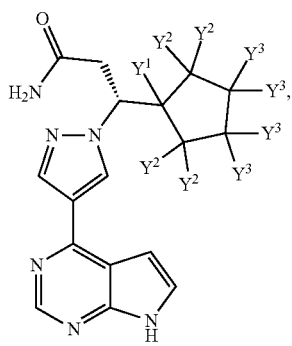

or a pharmaceutically acceptable salt thereof,
wherein,
$Y^1$ is selected from hydrogen and deuterium;
each $Y^2$ is selected from hydrogen and deuterium; and
each $Y^3$ is selected from hydrogen and deuterium
wherein each position designated specifically as deuterium has at least 90% deuterium incorporation; (ii) a second JAK inhibitor; and (iii) a pharmaceutically acceptable carrier.

20. The method of claim 19, wherein the second JAK inhibitor is selected from CTP-543, ruxolitinib, tofacitinib, baricitinib, upadacitinib, fedratinib, filgotinib, momelotinib, pacritinib, itacitinib, peficitinib, PF-06651600, PF-06700841 (brepocitinib), and abrocitinib, and pharmaceutically acceptable salts thereof.

21. The method of claim 19, wherein the compound of Formula (I) is

Compound 10

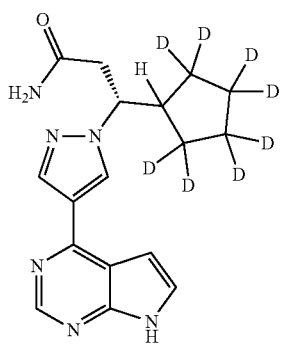

or a pharmaceutically acceptable salt thereof, and the second JAK inhibitor is CTP-543, or a pharmaceutically acceptable salt thereof.

22. The method of claim 21, wherein the pharmaceutical composition is administered at 16 mg/day or 24 mg/day of the first JAK inhibitor and the second JAK inhibitor together.

23. The compound of claim 3, wherein the pharmaceutically acceptable salt is a phosphate salt.

24. The method of claim 21, wherein the pharmaceutically acceptable salt is a phosphate salt.

* * * * *